(12) United States Patent
Bartish, Jr. et al.

(10) Patent No.: US 8,021,428 B2
(45) Date of Patent: Sep. 20, 2011

(54) CERAMIC DISC PROSTHESIS

(75) Inventors: Charles M. Bartish, Jr., Providence, RI (US); Jeffrey Brousseau, Barrington, RI (US); Patrick Fatyol, Whitman, MA (US); Conor McCrea, Dedham, MA (US); Michael J. O'Neil, West Barnstable, MA (US); Stephen Connolly, Sharon, MA (US)

(73) Assignee: DePuy Spine, Inc., Raynham, MA (US)

( * ) Notice: Subject to any disclaimer, the term of this patent is extended or adjusted under 35 U.S.C. 154(b) by 1243 days.

(21) Appl. No.: 10/908,766

(22) Filed: May 25, 2005

(65) Prior Publication Data

US 2006/0004453 A1    Jan. 5, 2006

Related U.S. Application Data

(60) Provisional application No. 60/584,054, filed on Jun. 30, 2004.

(51) Int. Cl.
*A61F 2/44* (2006.01)
(52) U.S. Cl. ............... 623/17.15; 623/17.16; 606/297
(58) Field of Classification Search .............. None
See application file for complete search history.

(56) References Cited

U.S. PATENT DOCUMENTS

| | | | |
|---|---|---|---|
| 4,743,260 A | 5/1988 | Burton | |
| 5,037,438 A | 8/1991 | Davidson | |
| 5,092,866 A | 3/1992 | Breard | |
| 5,258,031 A | 11/1993 | Salib et al. | |
| 5,282,863 A | 2/1994 | Burton | |
| 5,387,213 A | 2/1995 | Breard et al. | |
| 5,415,661 A | 5/1995 | Holmes | |
| 5,425,773 A | 6/1995 | Boyd et al. | |
| 5,474,086 A | 12/1995 | McCormick et al. | |
| 5,534,029 A | 7/1996 | Shima | |
| 5,540,688 A | 7/1996 | Navas | |
| 5,556,431 A | 9/1996 | Buttner-Janz | |
| 5,562,737 A | 10/1996 | Graf | |
| 5,562,738 A | 10/1996 | Boyd et al. | |
| 5,571,191 A | 11/1996 | Fitz | |
| 5,672,175 A | 9/1997 | Martin | |

(Continued)

FOREIGN PATENT DOCUMENTS

EP    0669109    2/1994

(Continued)

OTHER PUBLICATIONS

Int'l Search Report.

(Continued)

*Primary Examiner* — David H Willse
*Assistant Examiner* — Javier G Blanco
(74) *Attorney, Agent, or Firm* — Nutter McClennen & Fish LLP (57) ABSTRACT

A prosthetic is provided for replacing a vertebral disc. The prosthesis can comprise first and second endplates formed of a ceramic material, each including an articulating contact surface and a bone facing surface. The contact surface of the first endplate can have a shape complementary to the contact surface of the second endplate, thereby facilitating articulation of the first and second endplates while in contact with one another. The device can further include at least one non-ceramic bone attachment element mated with at least one of the bone facing surfaces, such that the bone attachment element covers less than a full area of the bone facing surface.

16 Claims, 10 Drawing Sheets

U.S. PATENT DOCUMENTS

| | | |
|---|---|---|
| 5,676,701 A | 10/1997 | Yuan et al. |
| 5,895,428 A | 4/1999 | Berry |
| 5,899,941 A | 5/1999 | Nishijima et al. |
| RE36,221 E | 6/1999 | Breard et al. |
| 5,961,516 A | 10/1999 | Graf |
| 6,039,763 A | 3/2000 | Shelekov |
| 6,063,121 A * | 5/2000 | Xavier et al. ............. 623/17.15 |
| RE36,758 E | 6/2000 | Fitz |
| 6,132,464 A | 10/2000 | Martin |
| 6,146,421 A | 11/2000 | Gordon et al. |
| 6,228,118 B1 | 5/2001 | Gordon |
| 6,267,764 B1 | 7/2001 | Elberg |
| 6,273,888 B1 | 8/2001 | Justis |
| 6,368,350 B1 | 4/2002 | Erickson et al. |
| 6,419,703 B1 | 7/2002 | Fallin |
| 6,517,580 B1 | 2/2003 | Ramadan et al. |
| 6,527,803 B1 * | 3/2003 | Crozet et al. .............. 623/17.11 |
| 6,554,831 B1 | 4/2003 | Rivard et al. |
| 6,565,605 B2 | 5/2003 | Goble |
| 6,579,319 B2 | 6/2003 | Goble |
| 6,579,321 B1 | 6/2003 | Gordon et al. |
| 6,610,091 B1 | 8/2003 | Reiley |
| 6,645,207 B2 | 11/2003 | Dixon |
| 6,669,729 B2 | 12/2003 | Chin |
| 6,706,068 B2 | 3/2004 | Ferree |
| 6,811,567 B2 | 11/2004 | Reiley |
| 6,994,727 B2 | 2/2006 | Khandkar et al. |
| 7,060,099 B2 | 6/2006 | Carli et al. |
| 7,179,294 B2 | 2/2007 | Eisermann et al. |
| 7,235,101 B2 * | 6/2007 | Berry et al. ................ 623/17.11 |
| 7,331,994 B2 | 2/2008 | Gordon et al. |
| 2002/0065557 A1 | 5/2002 | Goble et al. |
| 2002/0072800 A1 | 6/2002 | Goble et al. |
| 2002/0123806 A1 | 9/2002 | Reiley |
| 2002/0133155 A1 | 9/2002 | Ferree |
| 2003/0004572 A1 | 1/2003 | Goble et al. |
| 2003/0028250 A1 | 2/2003 | Reiley et al. |
| 2003/0055427 A1 | 3/2003 | Graf |
| 2003/0083657 A1 | 5/2003 | Drewry |
| 2003/0109880 A1 | 6/2003 | Shirado et al. |
| 2003/0135277 A1 | 7/2003 | Bryan et al. |
| 2003/0135278 A1 * | 7/2003 | Eckman ..................... 623/17.14 |
| 2003/0153912 A1 | 8/2003 | Graf |
| 2003/0171749 A1 | 9/2003 | Le Couedic et al. |
| 2003/0171750 A1 | 9/2003 | Chin |
| 2003/0176922 A1 | 9/2003 | Lawson et al. |
| 2003/0191470 A1 | 10/2003 | Ritland |
| 2003/0191532 A1 | 10/2003 | Goble et al. |
| 2003/0220642 A1 | 11/2003 | Freudiger |
| 2003/0220643 A1 | 11/2003 | Ferree |
| 2004/0002708 A1 | 1/2004 | Ritland |
| 2004/0006391 A1 | 1/2004 | Reiley |
| 2004/0010316 A1 | 1/2004 | William et al. |
| 2004/0024462 A1 | 2/2004 | Ferree |
| 2004/0049189 A1 | 3/2004 | Le Couedic et al. |
| 2004/0049190 A1 | 3/2004 | Biedermann et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049281 A1 | 3/2004 | Reiley |
| 2004/0068318 A1 | 4/2004 | Coates et al. |
| 2004/0068320 A1 | 4/2004 | Robie |
| 2004/0073215 A1 | 4/2004 | Carli |
| 2004/0073311 A1 | 4/2004 | Ferree |
| 2004/0111154 A1 | 6/2004 | Reiley |
| 2004/0116927 A1 | 6/2004 | Graf |
| 2004/0143264 A1 | 7/2004 | McAfee |
| 2004/0186475 A1 | 9/2004 | Falahee |
| 2004/0236329 A1 | 11/2004 | Panjabi |
| 2005/0033431 A1 | 2/2005 | Gordon et al. |
| 2005/0033432 A1 | 2/2005 | Gordon et al. |
| 2005/0033439 A1 | 2/2005 | Gordon et al. |
| 2005/0080488 A1 | 4/2005 | Schultz |
| 2005/0101954 A1 | 5/2005 | Simonson |
| 2005/0101956 A1 | 5/2005 | Simonson |
| 2005/0113927 A1 | 5/2005 | Malek |
| 2005/0131544 A1 * | 6/2005 | Kuras et al. ................ 623/17.13 |
| 2005/0197702 A1 * | 9/2005 | Coppes et al. ............. 623/17.12 |

FOREIGN PATENT DOCUMENTS

| | | |
|---|---|---|
| JP | 63-164948 | 7/1988 |
| RU | 2 080 841 | 6/1997 |
| WO | WO-01/45576 | 6/2001 |
| WO | WO-02/17803 | 3/2002 |
| WO | WO-02/43603 | 6/2002 |
| WO | WO-02/102259 | 12/2002 |
| WO | WO-03/007828 | 1/2003 |
| WO | WO-03/009737 | 2/2003 |
| WO | WO 03039400 A2 * | 5/2003 |
| WO | WO-2004/024011 | 3/2004 |
| WO | WO-2004/034916 | 4/2004 |

OTHER PUBLICATIONS

Stoeckel, D., "Forming of Nitinol—A Challenge", New Developments in Forging Technology (ed.), K. Siegert, 2001, pp. 119-134.

* cited by examiner

CERAMIC DISC PROSTHESIS

CROSS REFERENCE TO RELATED APPLICATIONS

The present invention claims priority to U.S. Provisional Application Ser. No. 60/584,054, filed on Jun. 30, 2004 and entitled "Ceramic Artificial Disc," which is hereby incorporated by reference in its entirety.

BACKGROUND OF THE INVENTION

Disease, advancing age, and trauma can lead to changes in various bones, discs, joints, and ligaments of the body. Some changes manifest themselves in the form of damage or degeneration to a spinal disc. It is known that an intervertebral disc can be subject to damage, such as compression, deformation, displacement, or wear, and more generally degeneration associated with the mechanical stresses that are applied thereto and that lead to anatomical and functional destruction of the disc and of the vertebral segment. This damage to the disc alters its mechanical behavior and causes instability which can, in turn, give rise to a painful osteoarthritic reaction.

This pain can sometimes be eliminated by spinal fusion in which two adjacent vertebral bodies are joined together after removing the intervening intervertebral disc. A prosthetic device is usually placed between the two adjacent vertebral bodies, in place of the removed disc, to fill the space left by the removed disc and to allow bone to grow between the two vertebral bodies.

Alternatively, proposals have been made to replace the defective disc with an artificial disc that preserves the natural mobility between adjacent vertebral bodies. For example, such prostheses can include first and second plates for fixing to adjacent vertebral bodies and an articulating mechanism, such as a ball joint, interposed between the two plates. Although such prostheses makes it possible to restore an appropriate height to the intersomatic gap, the articulating mechanism of the prosthesis can be subject to high levels of friction, thus making it sensitive to wear.

Other artificial discs include ceramic bearing surfaces positioned within titanium endplates. While the ceramic materials reduce wear, these implants are limited by small bearing surfaces. In addition, mounting stiff ceramic inserts into titanium endplates can generate high stresses in the ceramic material and cause disc failure. Thick titanium endplates can also interfere with post-operative imaging, an important diagnostic tool.

Despite known prostheses for the replacement of discs, there remains a need for additional prostheses that are sufficiently wear resistant, compatible with post-operative imaging, and suitable for secure and effective implantation within a patient's spine.

SUMMARY OF THE INVENTION

The present invention provides a disc prosthesis that features superior wear properties. The disc prosthesis is formed entirely or predominately of ceramic material, thus optimizing post-operative imaging. In one embodiment, the present invention provides an implantable prosthetic device for replacing spinal discs. The device includes first and second endplates each having an articulating contact surface and a bone facing surface. At least one of the first and second endplates is formed of a ceramic material. The contact surface of the first endplate has a shape complementary to the contact surface of the second end plate, such that when the endplates are in contact with each other, the contact surface of the first endplate can articulate with respect to the contact surface of the second endplate.

In another aspect, at least one non-ceramic bone attachment element is formed on or mated with at least one of the bone facing surfaces, such that the bone attachment element covers less than a full area of the bone facing surface. The bone attachment element can include bone-penetrating teeth formed from a material selected from the group consisting of a metal, a plastic, and combinations thereof. When positioned within a vertebral column, the bone-penetrating teeth are effective to resist retropulsion.

In another aspect, the bone attachment element includes bone penetrating teeth formed from a shape memory material. The teeth can be positioned substantially parallel to the bone facing surface before activation and orientated to penetrate bone after activation.

The disc prosthesis device can further include a mating element for mating with an insertion tool. In one aspect, the device includes a male mating element adapted to mate with an insertion tool. In another aspect, the mating element is positioned on the bone attachment element and is adapted to mate with a male or female insertion tool.

In another embodiment of the disc prosthesis device disclosed herein, the first and second endplates are formed of a ceramic material and each have an articulating surface and an opposed bone contacting surface. The articulating surfaces are complementary to each other such that the first and second endplates can articulate while in contact with one another and are unconstrained in their relative movement by any portion of the prosthesis. The device may also include bone penetrating features positioned on at least one of the bone facing surfaces.

In a further aspect, the device disclosed herein includes a coating that encourages bone in-growth and/or bone adhesion. For example, at least one of the bone contacting surfaces can includes a coating of a particulate ceramic or another biocompatible material that provides a porous surface for bone in-growth.

In another embodiment, a method of implanting a disc prosthesis is disclosed, in which there is provided a disc prosthesis having first and second endplates, each including an articulating surface and an opposed bone facing surface. At least one of the bone facing surfaces can have a bone attachment element formed from a heat-activated shape memory material. The method further includes the step of inserting the disc prosthesis between two vertebral bodies wherein the bone attachment element is in a first, non-bone penetrating orientation, and subjecting the bone attachment element to an activating force effective to orient the bone attachment element in a second, bone penetrating orientation.

In one aspect, the activating force is body heat. When the device is at room temperature, teeth on the bone attachment element are oriented to be positioned to lie against the surface of the device. Once the bone attachment element is heated to a sufficient degree, the teeth become reoriented into a bone penetrating position and resist retropulsion.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention provides a prosthesis that conserves vertebral function and provides wear resistant articulation surfaces. In one aspect, superior tribological wear properties are provided by forming at least a portion, and preferably all or substantially all, of the prosthesis from a ceramic material having sufficient strength to withstand in-vivo and insertion loading. Ceramic bearing surfaces provide excellent wear resistant properties that allow the device to articulate when positioned within a patient's spine such that at least some of the natural mobility between adjacent vertebral bodies is conserved. Ceramic materials are also compatible with post-operative imaging such that a surgeon can determine if the prosthesis is properly positioned and/or can asses the health of surrounding tissue and adjacent levels.

Figure 1:
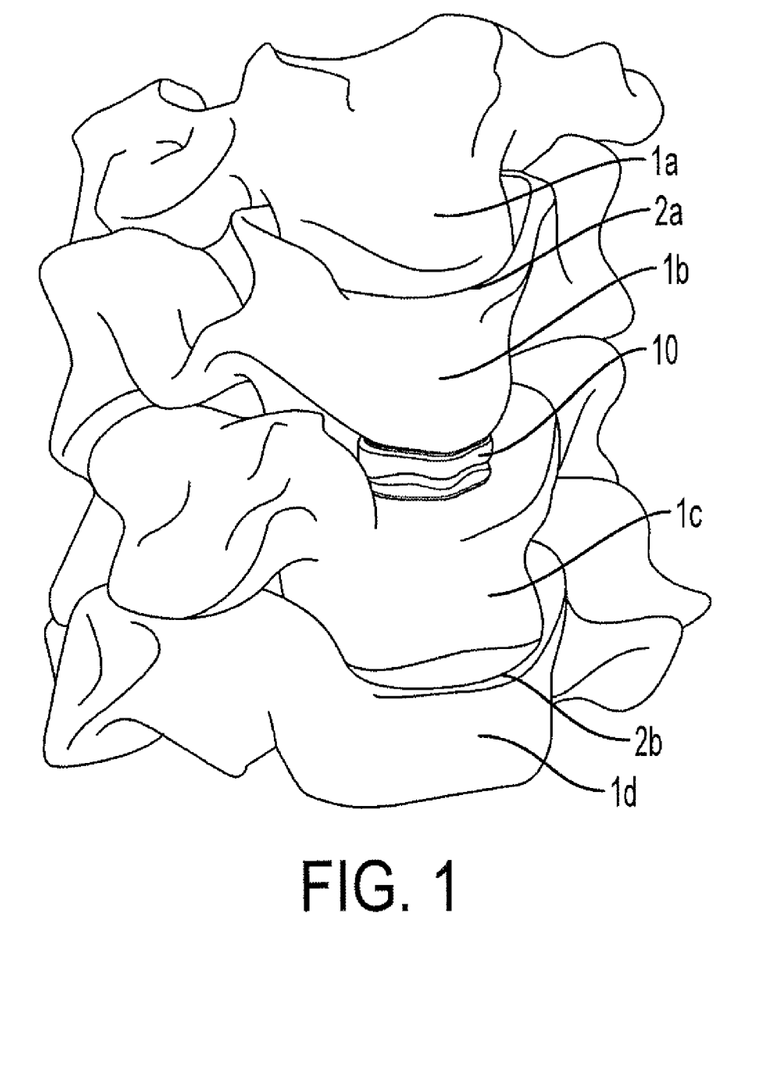
FIG. 1 is a perspective view of one embodiment of a prosthetic disc device positioned within a vertebral column.

FIG. 1 illustrates a perspective view of a portion of a vertebral column including vertebral bodies 1a, 1b, 1c, 1d, and natural discs 2a and 2b. A damaged disc between vertebral bodies 1b and 1c has been resected and replaced with a prosthetic disc 10 that has been inserted in the space created between the adjacent vertebral bodies (1b, 1c). As explained below, ceramic bearing surfaces of prosthesis 10 allow vertebral bodies 1b, 1c to maintain at least some degree of mobility. As further explained below, disc 10 can include bone mating surfaces, coatings, and/or bone penetrating elements, which together or separately, facilitate bone in-growth and help to fix the prosthesis in position.

Figure 2A:
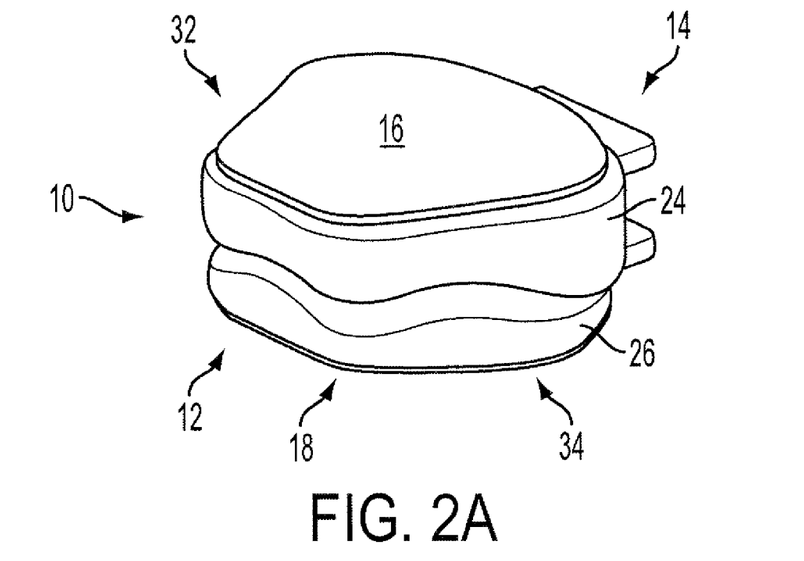
FIG. 2A is a perspective view of the prosthetic disc device according to one embodiment of the present invention.
Figure 2B:
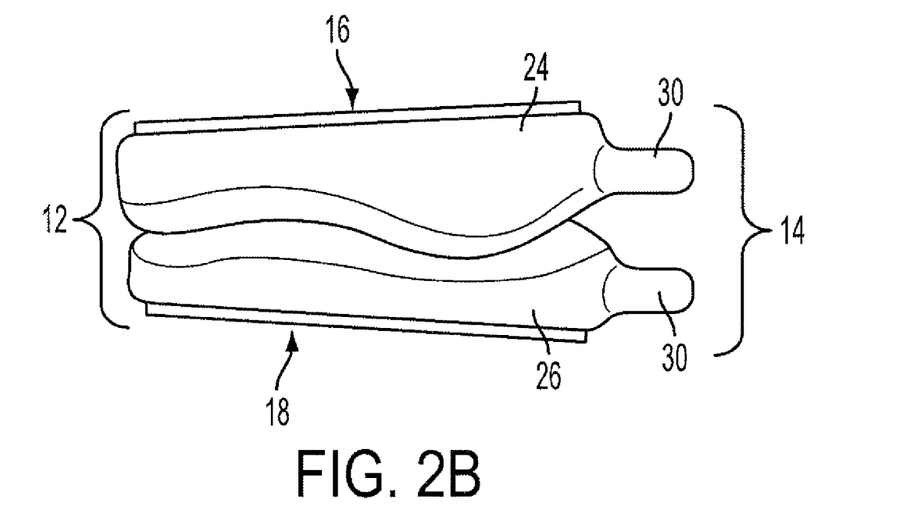
FIG. 2B is a side view of the prosthetic disc device of FIG. 2A.
Figure 2C:
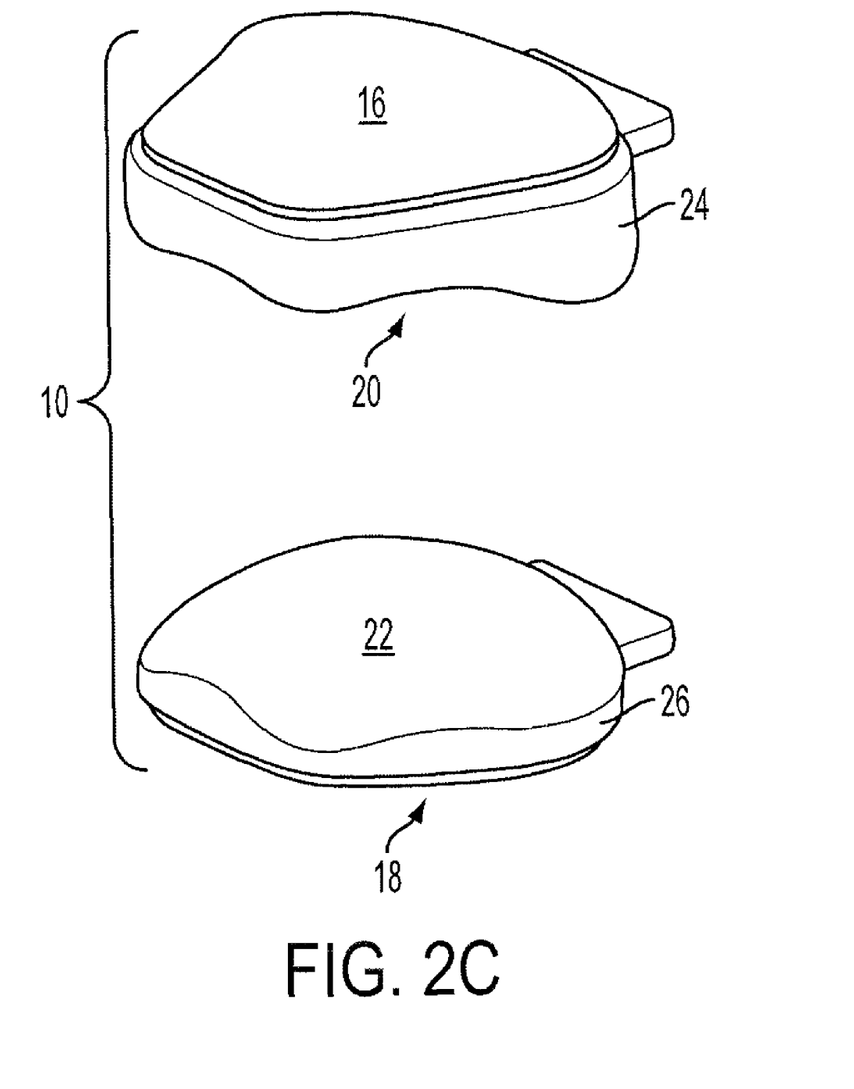
FIG. 2C is an exploded view of the prosthetic disc device of FIG. 2A.

Referring to FIGS. 2A through 2C, disc 10 in one aspect, includes first and second endplates 24, 26 each having an articulating contact surface 20, 22 and a bone facing surface 16, 18 where at least one of the first and second endplates is formed of a ceramic material. In one aspect, both endplates are formed entirely or substantially from ceramic materials.

As shown in FIGS. 2A through 2C, the prosthetic disc is generally shaped and sized for positioning between adjacent vertebral bodies and contacting the vertebral bodies. As shown, disc 10 can have a somewhat rectangular or trapezoidal shape with an anterior surface 14 and a posterior surface 12, and a superior surface 16 and an inferior surface 18. The superior 16 and inferior 18 surfaces are bone facing surfaces while interior surfaces 20, 22 (FIG. 2C) are articulating surfaces.

The sides of disc 10, including anterior surface 14 and posterior surface 12 can be shaped to match the anatomical configuration of the inter-vertebral space into which disc 10 is inserted. For example, posterior surface 12 can have a width shorter than that of the anterior surface 14, causing the width to taper from the posterior to the anterior. In addition, the corners of the prosthesis can be rounded to reduce the chance of the prosthesis causing trauma to surrounding tissue. The height of disc 10 is also adapted to be compatible with the anatomical structure of a vertebral column, and in particular, the height should be such that it provides the desired spacing between adjacent vertebrae.

Disc 10, in one aspect, is formed from a superior end plate 24 and an inferior endplate 26, each having a bone facing surface 16, 18 and an articulating contact surface 20, 22 that allow the endplates to move relative to one another. FIG. 2C shows an exploded view of disc 10 with articulating surface 22 of inferior endplate 26 adapted to articulate with articulating surface 20 of superior endplate 24. Articulating surfaces 20, 22 can have a variety of shapes that allow movement of the adjacent vertebra to which they are attached. In one aspect, articulating surfaces 20, 22 are complementary, with articulating surface 22 having a convex configuration that is received within a concave articulating surface 20. Articulating surfaces 20, 22 can be formed such that the movement of endplates 24 and 26 (and their respective vertebral bodies) is similar to the action of a natural vertebral disc. For example, the shape of articulating surfaces 20, 22 allows for flexion, extension, lateral bending, and/or rotational movement. One skilled in the art will appreciate that a variety of alternative articulating surface shapes that allow relative movement of the endplates can be used. In an alternative embodiment, articulation of endplates 24, 26 could be provided by a three-piece (or more) design. For example, a motile core could be positioned between endplates 24, 26. Other exemplary designs could include a ball-in-trough configuration.

In one aspect, endplates 24, 26 are configured such that relative movement is not limited or constrained by the structure of prosthetic disc 10. As the endplates move relative to one another they do not encounter another portion of disc 10 that limits the amount of flexion, extension, lateral bending, or rotational movement of the endplates. Once implanted, only the anatomy of the vertebral column and surrounding tissue, or other implants, limit movement of the endplates relative to one another.

Endplates 24, 26 can further include features for mating with an inserter tool (not shown). For example, a mating element 30 can extend from anterior surface 14 of at least one the endplates and be adapted for gripping by an inserter tool. As shown in FIGS. 2A through 2C, mating element 30, in one aspect, includes a male tab, having substantially flat upper and lower surfaces, that extends from the surface of each endplate 24, 26. Alternatively, an inserter tool could mate with a female mating element 30, including for example, a recess in the anterior surface 14 of disc 10. In another aspect, mating element 30 could be positioned on a side surface of prosthetic disc 10. For example, one or both of side surfaces 32, 34 of prosthetic disc 10 could include a slot within which an inserter tool could be seated.

Figure 3:
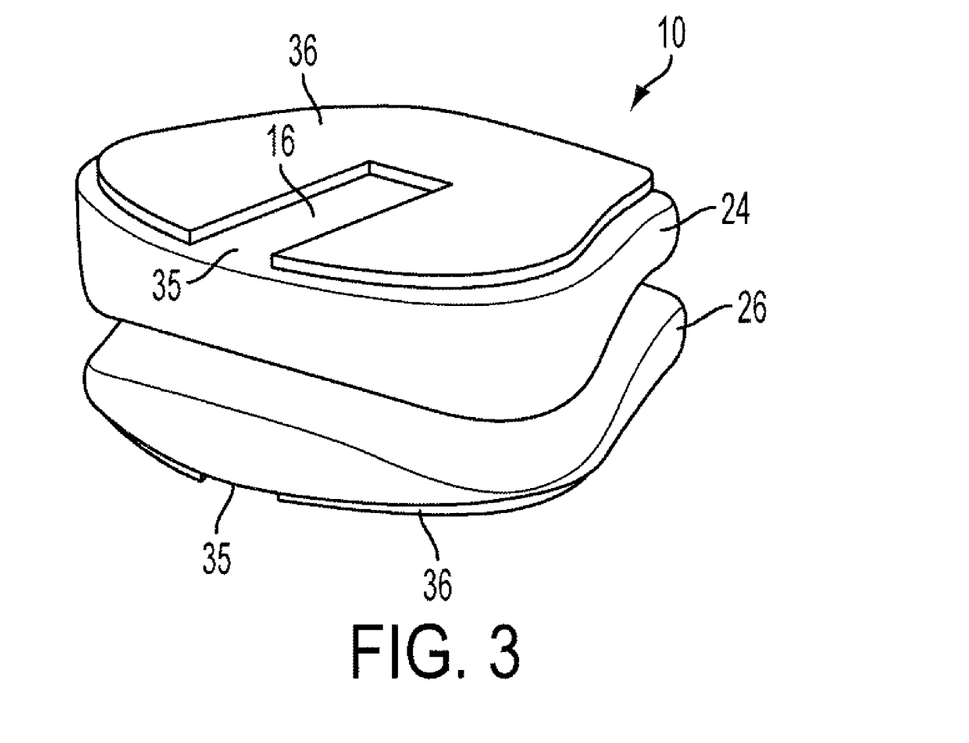
FIG. 3 is a perspective view of another embodiment of the prosthetic disc device.

In one embodiment, prosthetic disc 10 does not include an element particularly adapted for mating with an inserter tool. Instead, an inserter tool adapted to grip the surfaces of disc 10, such as, bone facing surfaces 16, 18; sides 32, 34; and/or anterior surface 14. In one aspect, an insertion tool can instead have a shape corresponding to the anterior end of disc 10 and include features for gripping surfaces 16, 18. FIG. 3 illustrates one embodiment of prosthetic disc 10 that includes area 35 on bone facing surfaces 16, 18 that can be engaged by an inserter tool. One skilled in the art will appreciate that a variety of inserter tools can be adapted to mate with disc 10.

The superior and inferior surfaces 16, 18 of prosthetic disc 10 are positioned to face the adjacent vertebral bodies between which they will be inserted. When positioned within the vertebral column these surfaces face the exposed bone of the adjacent vertebral bodies. In one aspect, these bone facing surfaces 16, 18 are bone contacting surfaces and are adapted to mate with bone. Once inserted within the vertebral column, the surfaces 16, 18 contact the adjacent vertebral bodies and, over time, the disc is secured through osteointegration as bone grows into the ceramic material that forms the disc. Surfaces 16, 18 can also include features, such as porous regions and/or recesses to enhance and facilitate bone in-growth.

In one embodiment, porous regions on the bone facing surfaces are provided by a coating 36 that fosters bone growth and/or bone adhesion. In one aspect, coating 36, shown in FIG. 3, could be positioned on surfaces 16, 18 to provide a rough and/or porous structure into which bone can grow. For example, coating 36 could be formed from particles of ceramic material. Coating 36 could include a variety of other materials such as binders (e.g., an adhesive) and/or biologically active materials that encourage bone in-growth. Exemplary materials include calcium phosphate, hydroxy apatite, plasma sprayed titanium beads, plasma sprayed CCM and combinations thereof. As explained below in more detail, surfaces 16, 18 can also, or alternatively, include one or more bone attachment elements to help secure disc 10 to bone.

Endplates 24, 26 can be formed from a variety of ceramic materials. Exemplary materials include alumina, zirconia, yttria, and blends thereof. One skilled in the art will appreciate that a variety of ceramic materials having low friction, wear resistant properties can be used to form endplates 24, 26. For example, ceramics such as Ceramtec's, Biolox® Delta material or Amedica's, $MC^2$ can be used.

In another embodiment of prosthetic disc 10, a non-ceramic bone attachment element 38, 38', 38", 38''', 38'''' is positioned on one or both of the bone facing surfaces 16, 18. While ceramic materials are very hard and have low wear characteristics, forming bone penetrating members (e.g., spikes or teeth) from ceramic can be difficult because ceramic is brittle. To avoid this problem, bone attachment elements 38, 38', 38", 38''', 38'''' can provide bone penetrating spikes or teeth 40, 40', 40" formed of a non-ceramic material. The spikes or teeth 40, 40', 40" penetrate and/or engage bone to prevent disc 10 from moving out of position once implanted. In addition, non-ceramic bone attachment elements can help to evenly distribute forces across the bone facing surfaces of the endplates.

Bone attachment element 38, 38', 38", 38''', 38'''' can be formed from a variety of non-ceramic materials such as metals and plastics. For example, the bone attachment element could be formed from a strip of metal, such as stainless steel, titanium, or another biocompatible metal that is stamped or machined. Alternatively, the attachment element could be a rigid plastic such as, for example, carbon fiber reinforced plastics, polyetheretherketon, and/or other biocompatible plastics.

In one embodiment, bone attachment element 38, 38', 38", 38''', 38'''' is formed from a material that is at least partially compatible with an imaging technique, such as magnetic resonance imaging (MRI). This allows a surgeon to use post-operative imaging techniques to view the prosthesis and surrounding tissue, including soft tissue. Where the materials used to form the bone attachment element are partially compatible with post-operative imaging techniques, the bone attachment element is preferably small enough that it produces minimal interference with post-operative imaging.

Figure 11A:
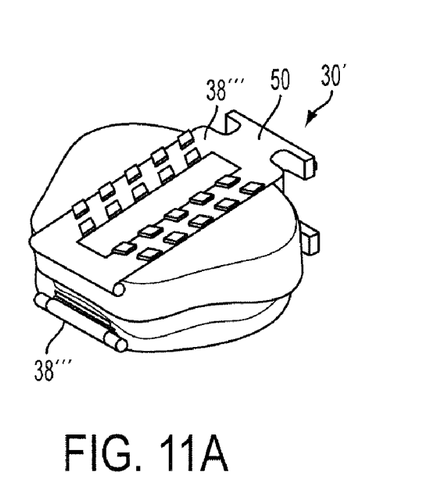
FIG. 11A is a perspective view of another embodiment of a prosthetic disc device.
Figure 11B:
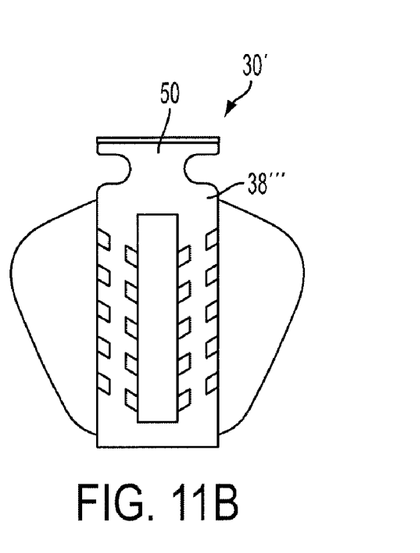
FIG. 11B is a top view of the prosthetic disc device of FIG. 11A.

FIGS. 4A through 5B illustrate exemplary embodiments of bone attachment elements 38 positioned on bone facing surfaces 16, 18 and having teeth adapted to penetrate bone. In one aspect, bone attachment elements 38 comprise two parallel strips of material with raised portions defining teeth 40. The bone attachment elements can be positioned, for example, with their axes $I_1$-$I_1$ and $I_2$-$I_2$ oriented in the anterior/posterior direction. While two bone attachment elements are positioned on each surface 16, 18 in FIGS. 4A through 5B, one skilled in the art will appreciate that disc 10 can include more than one bone attachment element per surface (e.g., three or more) or fewer (e.g., one). FIGS. 6A through 14 illustrate a variety of other exemplary configurations of the bone attachment elements. For example, the bone attachment element could be positioned around the perimeter of the bone facing surfaces (FIGS. 6A and 6B), across the entire surface of the bone facing surfaces (FIGS. 7A and 7B), in a cross configuration (FIGS. 9A and 9B), around the perimeter and across the center of the bone facing surfaces (FIGS. 10A and 10B), and as connected parallel strips (FIGS. 11A and 11B).

As noted above, attachment elements 38, 38', 38", 38''', 38'''' can cover less than the full area of bone facing surfaces 16, 18. A portion of the ceramic bone facing surfaces 16, 18 thus remain uncovered by bone attachment element 38, 38', 38", 38''', 38'''' and will accommodate bone in-growth. For example, FIGS. 5A through 6B and 8A through 14, illustrate disc 10 with at least a portion of bone facing surfaces 16, 18 uncovered by the bone attachment elements. In addition to facilitating bone in-growth, the small profile of the bone attachment elements can facilitate post-operative imaging. For example, where the bone attachment element is partially compatible with imaging techniques, covering only a portion of bone facing surfaces 16, 18 with the bone attachment element can minimize interference with post-operative imaging.

Bone attachment element 38, 38', 38", 38''', 38'''' can be fixed to prosthetic device 10 in a variety of ways, including, for example, brazing, adhesion, mechanical attachment, and combinations thereof. Endplates 24 and 26 can also include features, such as a recess to assist with attachment of the bone attachment element. In one embodiment, bone attachment element 38' is mated with disc prosthesis 10 by way of a mechanical interlock, such as, for example snap-fit, friction fit, tongue-and-groove, overmolding, overcasting, thermal interference fit, and combination thereof. In one aspect, shown in FIGS. 8A and 8B, the bone attachment element can mate or interlock with recesses 42 on the anterior and posterior surfaces 14, 12 of disc 10. The ends of bone attachment element 38' can be flexible and include a protrusion that snaps into recess 42.

In an alternative embodiment, shown in FIGS. 9A through 10B, bone attachment element 38" is seated within a recess in the bone facing surfaces (16, 18). For example, the bone attachment element could be flush with the bone facing surfaces 16, 18, such that surfaces 16, 18 are easily accessed by bone. FIGS. 9A through 10B also illustrate embodiments in which bone attachment element 38" is seated with a recess in the surfaces 16, 18 of the disc prosthesis. The bone attachment element can be mated within the recess in a variety of ways including, for example, mechanical interlock and adhesion. In one exemplary embodiment, the bone attachment element is formed within a recess. For example, polymer can be poured into a recess (e.g., an overhanging recess) in the bone facing surfaces 16, 18 of disc prosthesis 10 and then hardened to form bone attachment element 38". Alternatively, attachment element 38" could be held on the bone facing surface(s) with an adhesive, such as, for example brazing, bone cement, and/or an epoxy.

Figure 11C:
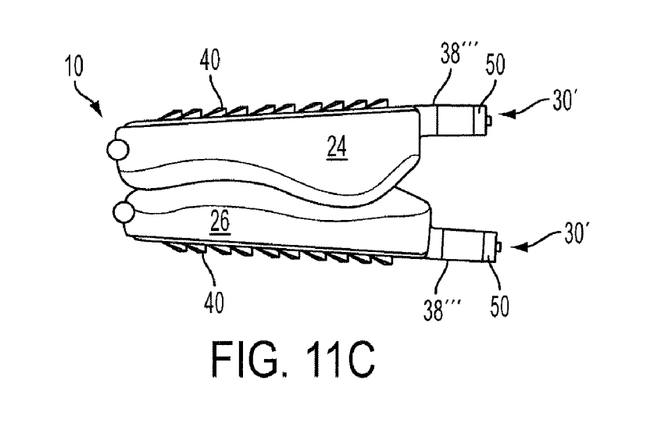
FIG. 11C is a side view of the prosthetic disc device of FIG. 11A.

In another embodiment of the disc 10, bone attachment element 38''', rather than endplates 24, 26, includes features for mating with an inserter tool. FIGS. 11A through 11C illustrate disc prosthesis 10 including mating element 30' defined by extension portion 50 formed integrally with bone attachment element 38'''. Instead of an inserter tool mating with the ceramic of the endplates 24, 26, the inserter tool can mate with the non-ceramic bone attachment element 38'''. As shown in FIGS. 11A through 11C, extension portion 50 can have a "T" shape and extend from the anterior portion of the prosthetic disc. In one aspect, extension portions 50 are positioned on bone mating elements 38'''.

If damage occurs to one of the endplates, it is usually during the insertion process because of the force required to implant the prosthetic disc between adjacent vertebral bodies. Accordingly, the bone attachment elements 38''' can be designed to break away if the strain during insertion approaches a force which can break the ceramic endplates. For example, extension portion 50 can have a built in fault that will fracture prior to the ceramic endplates breaking. Alternatively, extension portion 50 can be constructed of materials that will give way prior to reaching a threshold force.

Teeth 40, positioned on bone attachment element 38, 38', 38", 38''', 38'''', can be positioned at an angle with respect to the bone facing surfaces 16, 18 of disc 10, such that the teeth are driven into bone by retropulsive forces acting on the disc. The angle of teeth 40 with respect to the bone facing surface of the endplate can be in the range of about 5° and 75°, and preferably in the range of about 30° and 70°. In one embodiment, teeth 40 are formed from a ridged material and are fixedly positioned. Teeth 40 can alternatively be flexible to facilitate insertion such that they are pushed down (i.e., retracted or flattened) during insertion. Once the disc is inserted, the teeth will press against the bone to resist retropulsion.

Figure 4A:
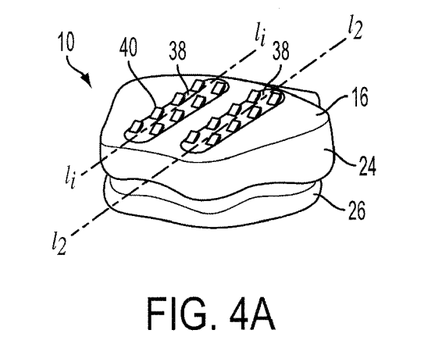
FIG. 4A is a perspective view of still another embodiment of the prosthetic disc device including a bone attachment element.
Figure 4B:
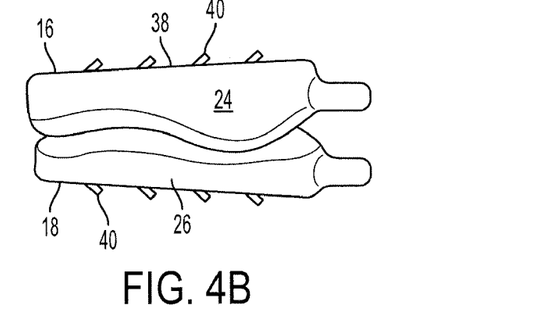
FIG. 4B is a side view of the prosthetic disc device of FIG. 4A.
Figure 5A:
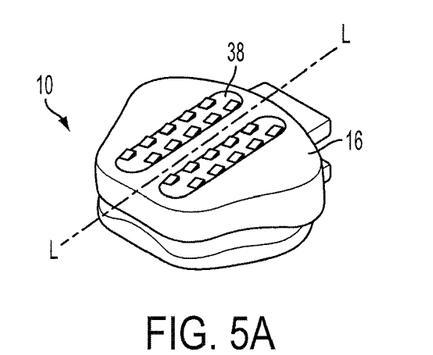
FIG. 5A is a perspective view of a prosthetic disc device with another embodiment of the bone attachment element.
Figure 5B:
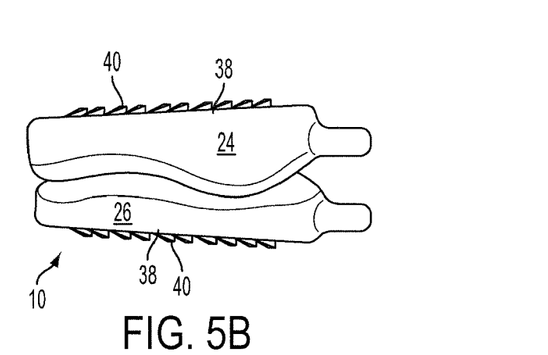
FIG. 5B is a side view of the prosthetic disc device of FIG. 5A.
Figure 6A:
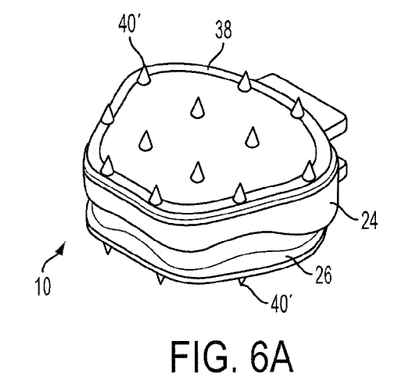
FIG. 6A is a perspective view of another embodiment of the prosthetic disc device.
Figure 6B:
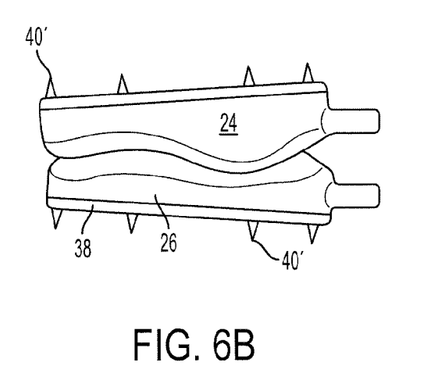
FIG. 6B is a side view of the prosthetic disc device of FIG. 6A.
Figure 7A:
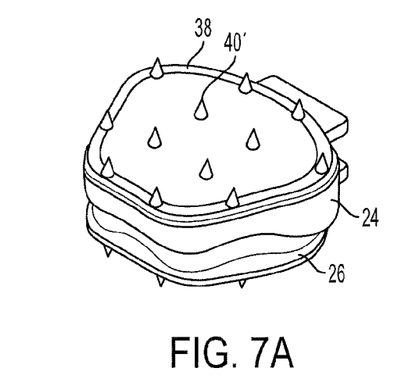
FIG. 7A is a perspective view of yet another embodiment of the prosthetic disc device.
Figure 7B:
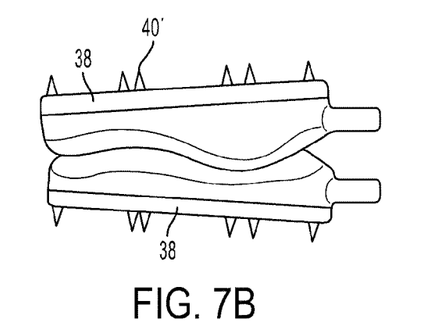
FIG. 7B is a side view of the prosthetic disc device of FIG. 7A.
Figure 8A:
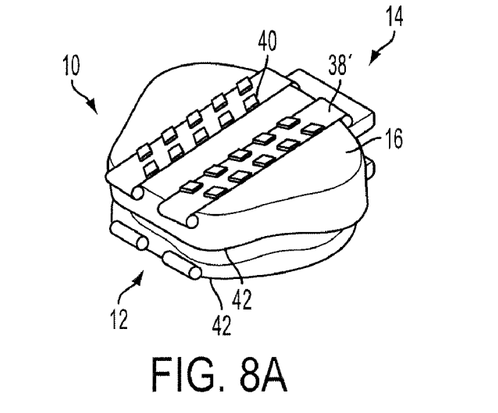
FIG. 8A is a view of the prosthetic disc device with a snap-on bone attachment element.
Figure 8B:
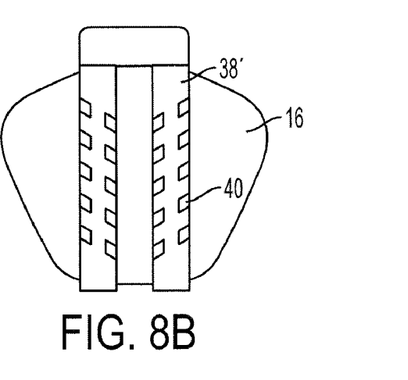
FIG. 8B is a top view of the prosthetic disc device of FIG. 8A.
Figure 9A:
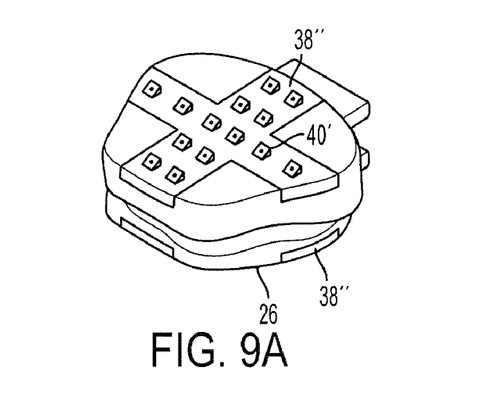
FIG. 9A is a perspective view of the prosthetic disc device with a bone attachment element seated within a recess in a bone facing surface.
Figure 9B:
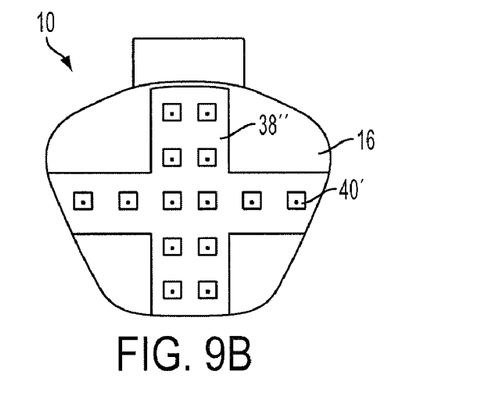
FIG. 9B is a top view of the prosthetic disc device of FIG. 9A.
Figure 10A:
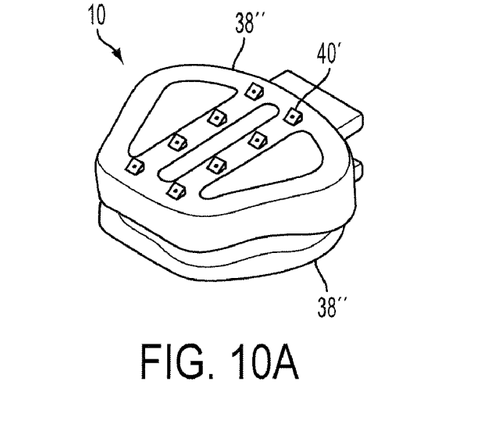
FIG. 10A is a perspective view of another embodiment of the prosthetic disc device having a bone attachment element seated within a recess of the bone facing surface.
Figure 10B:
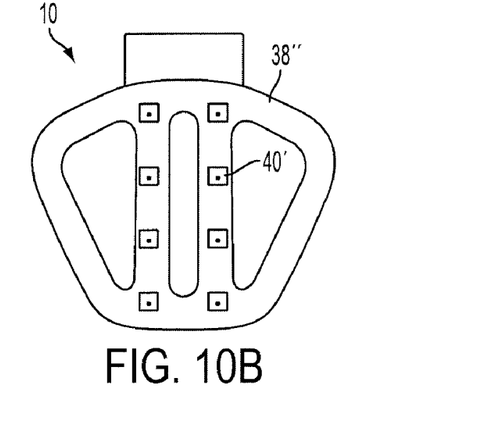
FIG. 10B is a top view of the prosthetic disc device of FIG. 10A.

One skilled in the art will appreciate that teeth 40 can have a size, shape, and orientation that will be effective to resist removal or migration of disc 10. In FIGS. 4A and 4B the teeth are unidirectional and are inclined in the posterior-anterior direction. Teeth 40 will not grab bone as disc 10 is inserted, but will resist retropulsion once the disc is inserted. Alternatively, the teeth can be positioned at an angle with respect to the direction of insertion. For example, teeth 40 can be angled with respect to the axis L-L shown in FIG. 5A. This orientation helps to prevent lateral movement of the prosthetic disc.

In another embodiment, disc 10 includes rigid teeth 40' which can extend in the superior/inferior direction. Teeth 40' can penetrate bone to hold disc 10 in place after insertion. For example, FIGS. 6A through 7B illustrate rigid teeth 40' positioned on a single bone attachment element. Movement of the disc in any direction will be resisted by the engagement of the teeth into bone.

In yet another embodiment of the disc prosthesis described herein, bone attachment element 38'''' is formed from a shape memory material. When activated, the bone attachment element can move from a non-bone penetrating configuration to a bone penetrating configuration. In one aspect, the shape memory material is heat activated and once inserted into a vertebral column, heat (e.g., body heat and/or a supplemental heat source) activates the shape memory material. When activated, bone penetrating teeth 40" on bone attachment element 38'''' move from a lowered position to an active, raised position.

Figure 12:
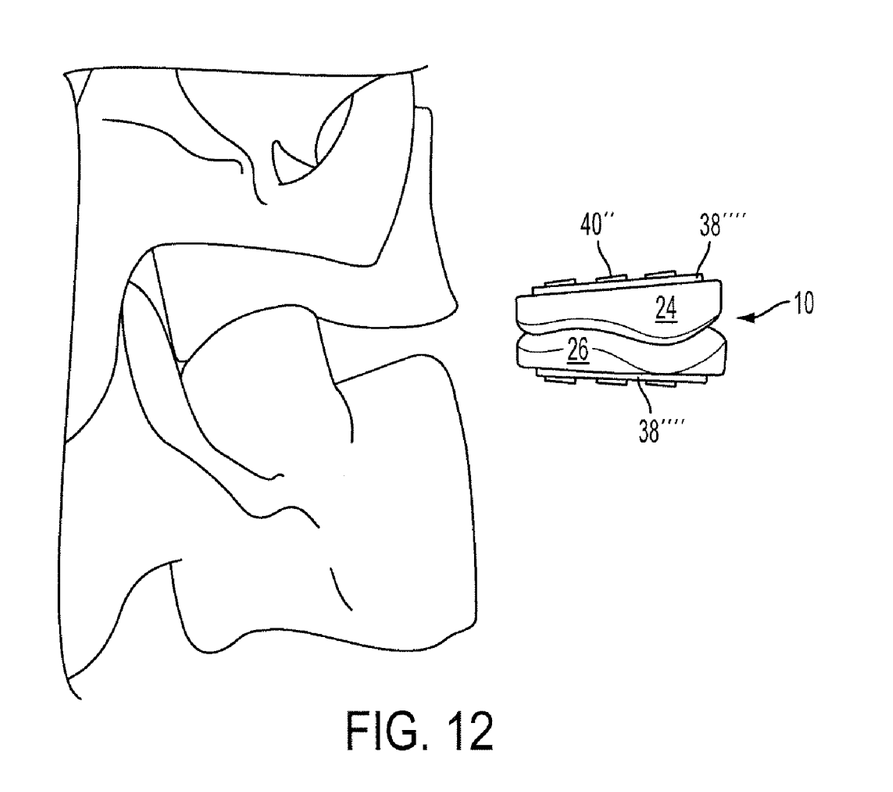
FIG. 12 is a side view of a prosthetic disc device in the process of being inserted between vertebral bodies of a vertebral column.
Figure 13A:
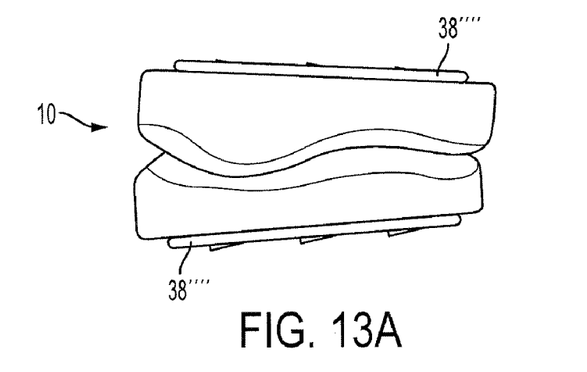
FIG. 13A is a side view of the prosthetic disc device with the bone attachment element in the non-bone penetrating position.
Figure 13B:
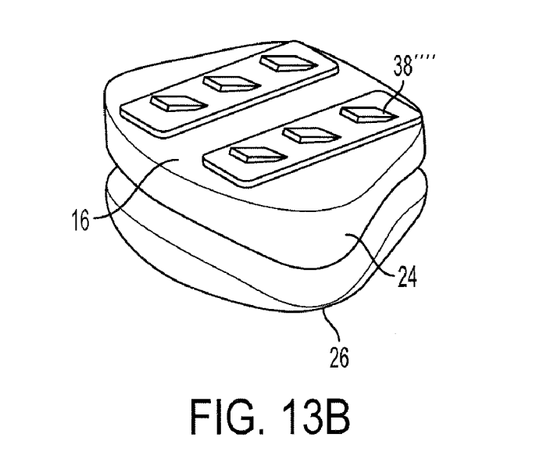
FIG. 13B is a perspective view of the prosthetic disc device of FIG. 13A.
Figure 14:
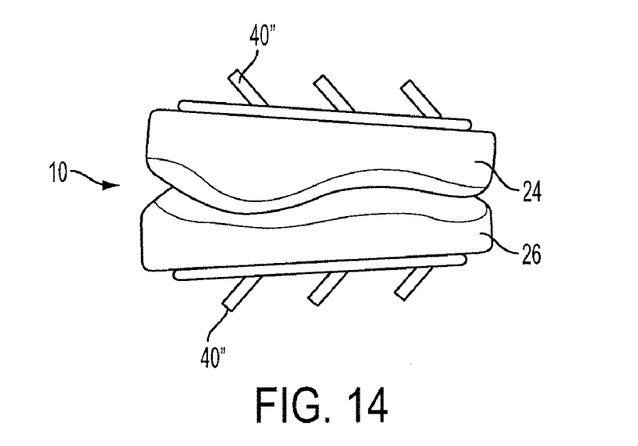
FIG. 14 is a side view of the prosthetic disc device of FIG. 13A with the bone attachment element in the bone penetrating position.

FIG. 12 illustrates a vertebral column with disc tissue removed and disc prosthesis 10 ready for insertion. As shown, teeth 40" are oriented in a low profile non-bone penetrating position. FIGS. 13A and 13B further illustrate disc 10 with teeth 40", formed of a shape memory material, in the non-bone engaging position. Disc 10 can be inserted with teeth 40" in their non-bone engaging position to facilitate insertion by reducing interference between teeth 40" and bone. Once disc 10 is positioned between vertebral bodies, bone attachment element 38'''' is activated by an activating force, such as body heat and/or a supplemental heat source, and teeth 40" become oriented in a bone engaging position as shown in FIG. 14A.

Bone attachment element 38'''' can be formed from the variety of shape memory materials. Exemplary materials include, for example, nickel-titanium intermetallic compounds (e.g., Nitinol) that exhibit thermal shape memory. Preferred materials include those that are activated at a temperature above room temperature, such as at, or slightly below, body temperature. In one embodiment, spike profiles are cut into a sheet of Nitinol and the sheet is heat treated so that the spikes will deploy (i.e., assume a bone penetrating position) at body temperature. Spikes 40" can lie substantially in the same plane as bone attachment elements 38'''' during implantations, then deploy into a raised, bone penetrating position once the disc is inserted.

One skilled in the art will appreciate that shape memory material based bone penetrating features can assume numerous configurations. In an alternative embodiment, the bone attachment elements can be in the form of bone engaging hooks (not shown), which can also be formed from a shape memory material. By way of example, the bone engaging elements can include wires when in the non-activated, non-bone penetrating condition. In the activated condition, for example, the wires may lie substantially in the same plane as surfaces 16, 18. Upon activation by an activating force, the wires are transformed into hooks that penetrate and/or securely engage bone.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A disc prosthesis device comprising:
first and second endplates each having an articulating contact surface and a bone facing surface, the contact surface of the first endplate has a shape complementary to the contact surface of the second endplate such that the first and second endplates can articulate while in contact with one another, at least one of the first and second endplates consisting of a ceramic material; and
at least one non-ceramic bone attachment element in the form of a longitudinal strip seated within a recess formed in at least one of the bone facing surfaces such that the bone attachment element covers less than a full area of the bone facing surface and sits flush with the bone facing surface, the at least one non-ceramic bone attachment element including a plurality of bone-penetrating teeth extending therefrom, the plurality of bone-penetrating teeth extending parallel to one another and along a longitudinal axis of the longitudinal strip, and wherein the plurality of bone-penetrating teeth are oriented and adapted so as to be compressed during insertion.

2. The device of claim 1, wherein the bone-penetrating teeth are formed from a material selected from the group consisting of a metal, a plastic, and combinations thereof.

3. The device of claim 1, wherein the teeth are oriented at an angle of less then 90° with respect to the bone facing surface.

4. The device of claim 1, wherein the plurality of bone-penetrating teeth are formed from a shape memory material.

5. The device of claim 4, wherein the teeth are oriented in a non-bone penetrating position before activation and are orientated at an inclined angle, and effective to penetrate bone after activation.

6. The device of claim 1, wherein the bone attachment element is mated to the endplate by a technique selected from the group consisting of bonding, mechanical interlock, brazing, overmolding, overcasting, thermal interference, and combinations thereof.

7. The device of claim 1, wherein the bone attachment element includes a mating element adapted to mate with an insertion tool.

8. The device of claim 7, wherein the mating element is selected from the group consisting of a male mating element and a female mating element.

9. The device of claim 1, wherein the first and second endplates include mating elements adapted to mate with a male or female insertion tool.

10. The device of claim 1, wherein a coating is positioned on at least one of the bone facing surfaces.

11. The device of claim 1, wherein a coating is positioned on the at least one bone attachment element.

12. The device of claim 1, wherein the plurality of bone-penetrating teeth extend in parallel rows.

13. A disc prosthesis comprising:
first and second endplates consisting of a ceramic material, the first and second endplates having an articulating surface configured to articulate relative to one another and opposed bone contacting surfaces configured to be positioned in contact with an endplate of a vertebra, the contact surface of the first endplate has a shape complementary to the contact surface of the second endplate such that the first and second endplates can articulate while in contact with one another, wherein rotational movement of the first and second endplates relative to one another is unconstrained by any portion of the prosthesis; and
non-ceramic bone engaging features positioned on at least one of the bone facing surfaces and comprising at least one non-ceramic bone attachment element in the form of a longitudinal strip that includes a plurality of bone-penetrating teeth extending therefrom and extending along a longitudinal axis thereof, wherein the at least one non-ceramic bone attachment element is seated within a recess formed in at least one of the bone contacting surfaces such that the bone attachment element covers less than a full area of the bone contacting surface and sits flush with the bone facing surface, wherein the plurality of bone-penetrating teeth extend in parallel rows, and wherein the plurality of bone-penetrating teeth are oriented and adapted so as to be compressed during insertion.

14. The device of claim 13, wherein at least one of the bone contacting surfaces includes a coating.

15. The device of claim 13, wherein the articulating surfaces of the first and second endplates are complementary to each other such that the first and second endplates can articulate while in contact with one another.

16. The device of claim 13, wherein at least one of the first and second endplates includes a mating element adapted to mate with an insertion tool.

* * * * *